United States Patent
Ambrosia et al.

(10) Patent No.: US 8,412,305 B2
(45) Date of Patent: Apr. 2, 2013

(54) MOBILE MULTIPLE MODALITY CONTAINMENT SUITE

(75) Inventors: Michael G. Ambrosia, Cleveland Heights, OH (US); Dennis K. Everett, Seven Hills, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 450 days.

(21) Appl. No.: 12/675,429

(22) PCT Filed: Aug. 26, 2008

(86) PCT No.: PCT/IB2008/053437
§ 371 (c)(1),
(2), (4) Date: Feb. 26, 2010

(87) PCT Pub. No.: WO2009/037606
PCT Pub. Date: Mar. 26, 2009

(65) Prior Publication Data
US 2010/0217066 A1 Aug. 26, 2010

Related U.S. Application Data

(60) Provisional application No. 60/972,826, filed on Sep. 17, 2007.

(51) Int. Cl.
*A61B 5/00* (2006.01)
(52) U.S. Cl. ............................ 600/407; 600/21; 600/425
(58) Field of Classification Search .................. 600/407, 600/410, 425, 21; 296/24.38; 312/1
See application file for complete search history.

(56) References Cited

U.S. PATENT DOCUMENTS

| | | | |
|---|---|---|---|
| 5,606,970 A * | 3/1997 | Damadian | 600/415 |
| 6,001,057 A | 12/1999 | Bongiovanni et al. | |
| 6,798,201 B2 | 9/2004 | Kuth | |
| 7,167,001 B2 | 1/2007 | Gewiese | |
| 7,840,249 B2 * | 11/2010 | Wang et al. | 600/407 |
| 2005/0055905 A1 * | 3/2005 | Sayer | 52/204.1 |
| 2005/0114892 A1 * | 5/2005 | Chan | 725/63 |
| 2005/0200360 A1 | 9/2005 | Gewiese | |
| 2006/0260050 A1 | 11/2006 | Manzione | |
| 2007/0033889 A1 | 2/2007 | Manzione | |

FOREIGN PATENT DOCUMENTS

| | | |
|---|---|---|
| DE | 19639975 C1 | 5/1998 |
| DE | 102004007427 A1 | 9/2005 |
| EP | 1262146 A2 | 12/2002 |
| WO | 0105348 A1 | 1/2001 |
| WO | 2007036889 A2 | 4/2007 |

\* cited by examiner

*Primary Examiner* — Ruth S Smith (57) ABSTRACT

There are occasions when a medical facility has the need to image subject that have been contaminated with a hazardous or communicable chemical or biological agent. Occurrences of such conditions are often too remote to justify having diagnostic scanners dedicated to such imaging. A contaminated or "hot" chamber (20) interfaces with one or more uncontaminated imaging suites or "cold" chambers (22). The hot chamber (20) includes barrier walls (16) with selectively deployable containment tubes (14) that when deployed, are sealed with the barrier wall (16) and extend from the barrier wall into the gantry of the cold chamber scanners. The tubes (14) extend the hot chamber (20) can be extended into the cold chambers (22) for imaging while remaining sealed, isolating the hot subjects from the cold imaging equipment. The imagers can thus be used for both normal clinical scanning and hot patient scanning.

17 Claims, 10 Drawing Sheets

MOBILE MULTIPLE MODALITY CONTAINMENT SUITE

CROSS REFERENCE TO RELATED APPLICATIONS

This application claims the benefit of U.S. provisional application Ser. No. 60/972,826 filed Sep. 17, 2007, which is incorporated herein by reference.

The present application relates to the biohazard containment arts. It finds particular application in scanning contaminated patients in uncontaminated scanning devices without contaminating the scanning devices, and will be described with particular reference thereto.

Currently, it is difficult to accommodate contaminated subjects in a typical clinical setting. The equipment used becomes contaminated, and personnel are exposed to potentially deadly pathogens. If a subject that has been contaminated with some biohazardous substance requires a diagnostic image or treatment, the scanners used would have to be shut down to normal clinical use, and then decontaminated when the need for scanning contaminated subjects passes. This can be a long process, as it can take 24 hours or more to decontaminate a typical medical device suite after it has been contaminated. This causes significant downtime of the scanner. Moreover, decontaminating sensitive electronics can be problematic In responding to an event that requires off-site imaging, a mobile response unit that includes multiple diagnostic scanners can be deployed to create a field scanning facility. A problem arises, though, when one of the subjects presents a biological threat. That is, the subject cannot be imaged without contaminating the scanner. As with the clinical setting, once the scanner is contaminated, it is a long process to ensure that it is decontaminated and safe for use with other subjects. It is desirable to avoid contamination of the scanners themselves.

The present application provides a new and improved containment suite which overcomes the above-referenced problems and others.

In accordance with one aspect, an imaging suite is provided. The suite includes a potentially contaminated region and an uncontaminated region. A barrier wall separates the contaminated region from the uncontaminated region. The barrier wall includes an aperture. A selectively deployable containment tube is sealed to the barrier wall in a deployed configuration and extends from the contaminated region into the uncontaminated region. A gantry of a first medical device is located in the uncontaminated region with an imaging region that is substantially coaxial with a longitudinal axis of the containment tube. In the deployed configuration, the tube extends into the gantry. In an undeployed configuration, the gantry is available for uncontaminated subjects. A subject support inserts a potentially contaminated subject from the contaminated region into the containment tube and into the gantry.

In accordance with another aspect, a method of diagnostic imaging is provided. A containment tube is moved to a deployed configuration surrounding and extending from an aperture in a barrier wall into a gantry of a first device, which is located on an uncontaminated region of the barrier wall. A first subject is disposed on a subject support in a contaminated region. The subject support is moved at least partially into the containment tube to place at least a portion of the first subject in the gantry.

In accordance with another aspect, an imaging environment for imaging potentially hazardous subjects is provided. A hot chamber receives potentially contaminated subjects. The hot chamber includes at least one subject support for supporting a subject during a medical procedure and a plurality of barrier walls, each barrier wall having an aperture through which a portion of the subject support can pass. The hot chamber also includes a containment tube for each aperture of each barrier wall adapted to extend the contaminated chamber beyond the barrier walls while still maintaining a seal of the contaminated chamber. A plurality of mobile cold areas are isolated from potentially contaminated subjects. Each cold area includes a medical device having a gantry, each gantry being aligned with the containment tube such that the containment tube can extend the hot chamber into a region of interest of the medical device without contaminating the cold areas.

One advantage is that normal clinical scanners can be used to scan contaminated subjects without contaminating the scanners.

Another advantage lies in the ability to be used in either fixed or mobile settings.

Another advantage lies in the ability to respond to an emergency biohazard situation.

Another advantage lies in the ability to be used in a research setting.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 1:
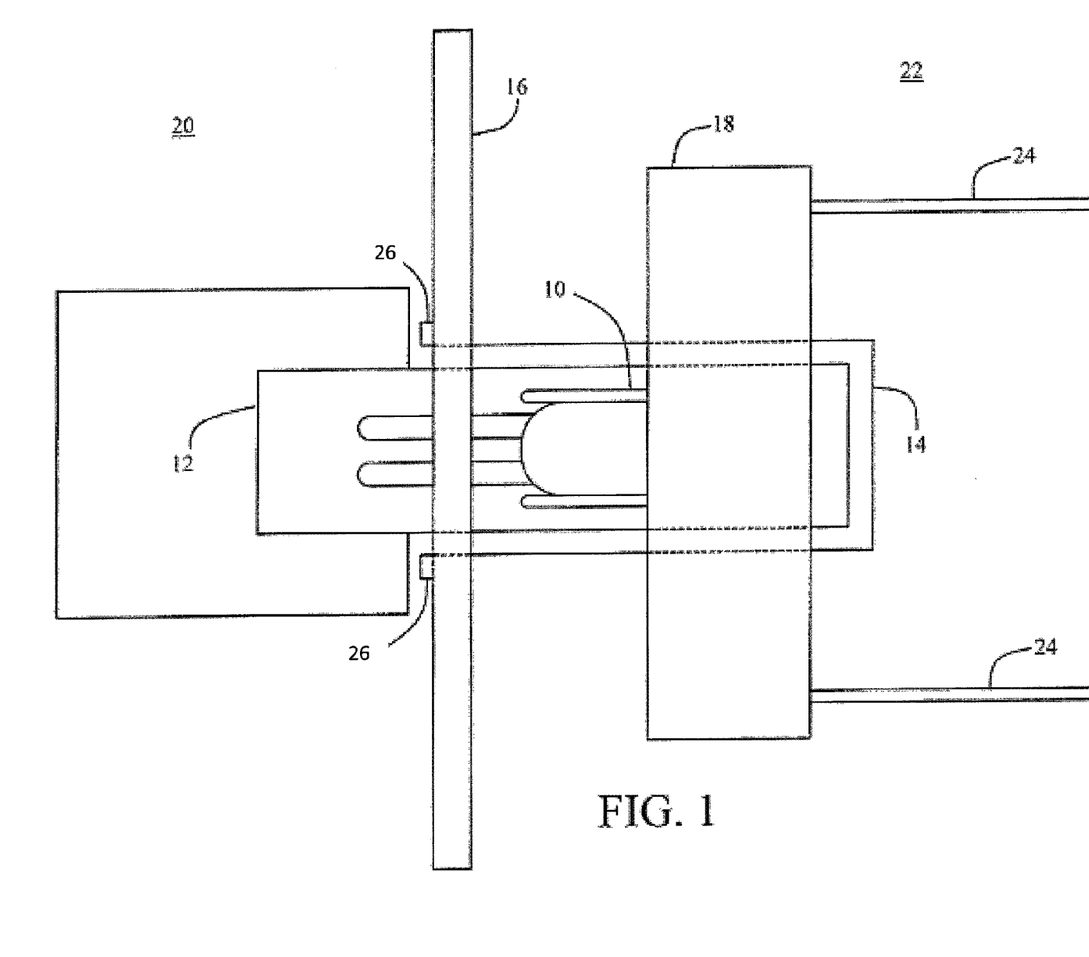
FIG. 1 is top down view of containment tube extending into an imaging gantry.

With reference to FIG. 1, a top down view of a containment setup is provided. Throughout this disclosure, "hot side" will be used to denote a contaminated region, while "hot" more generally describes the state of an object or location as being contaminated. The phrase "going hot," or a verbal derivative thereof, will be used to describe the act of contaminating a region or object. Conversely, "cold" shall refer to areas or objects that remain in their normal operating, uncontaminated states. Contamination could be the result of a terrorist act, a nuclear or industrial accident, medical testing or research, or the like.

A subject 10 located on a movable subject support 12 is shown extended into a containment vessel 14, such as a tube 14, through a barrier wall 16. Several embodiments of the containment vessel are described hereinbelow, but is to be understood that other vessels 14 are contemplated. The subject 10 is shown partially within a gantry 18 of a medical device, such as a diagnostic imaging device. It is to be understood, however, that the medical device can be other than an imaging device, such as a radiation treatment linac, or other device. The subject 10 and the subject support 12 are located on a hot side 20 of the barrier wall 16 while the gantry 18 is located on a cold side 22 of the barrier wall. The containment tube 14 extends the hot side 20 into the bore of the gantry 18 so that the subject 10 may be imaged by the diagnostic imaging device without contaminating the device or any of the rest of the imaging suite. A longitudinal axis of the tube 14 and the bore of the gantry are substantially coaxial so that the tube 14 fits into the bore. While the diagnostic imaging device is shown as having a gantry 18 for modalities such as MRI, CT, PET, and the like, it is to be understood that other modalities such as x-ray, fluoroscopy, and other modalities typically without bore-like gantries are also usable in conjunction with the containment tube 14. Ideally, to accommodate all different modalities, the tube 14 is made out of a material that is transparent to the various modalities. The gantry 18 is located on rails 24 that allow the gantry 18 to slide closer to the barrier wall 16 to facilitate imaging or treating potentially contaminated subjects 10 on the hot side 20 and further from the barrier wall 16 to facilitate imaging or treating subjects 10 on the cold side 22.

In one embodiment, the containment tube is detachably connected to the barrier wall 16. While in place, the containment tube 14 supports a BSL-4 containment level. A sealing interface 26 secures the containment tube 14 to the barrier wall 16. The cold side 22 is maintained at a higher pressure than the hot side 20. The interface 26 permits a controlled flow from the cold side 22 to the hot side 20. In the depicted embodiment, before either side goes hot, the tube 14 is inserted into the aperture in the containment wall from the side that will become the hot side 20 and secured into place. In this embodiment, the tube 14 remains in place after the hot side 20 goes hot, as removal of the tube 14 while the hot side 20 is contaminated will in turn contaminate the cold side 22.

After the biological containment event has run its course, and containment is no longer needed, the hot side 20 is decontaminated. Again, decontamination is performed with the containment tube 14 in place so as not to contaminate the cold side 22. Chemical aerosol decontaminates, pressurized steam, foams, and other decontaminates are contemplated. As it is intended that all the equipment that goes hot during the biological event will be reused multiple times, the parts are resilient to the selected decontaminate. Namely the patient support 12 the barrier wall 16 and the containment tube 14 can withstand multiple cleanings and decontaminations without having to be replaced, and are preferably inert to various potential decontaminates as may be appropriate for neutralizing any of a range of biological and chemical contaminants. For ease of decontamination and sterilization, the hot side 20 has rounded edges, minimizing corners and crevices where contaminants can lodge. All of the structures in the hot side 20 could be coated with an epoxy resin to facilitate cleaning. HEPA filters and safety checks can also be built into the ventilation system to decrease risk of contamination.

In a situation where containment is not needed, that is, when both sides of the barrier wall 16 are cold, the patient support 12 can be used as an alternate access to the gantry 18 with or without the containment tube 14. This could be used, for example, to prepare one patient while imaging another patient on the regular clinical table.

Figure 2:
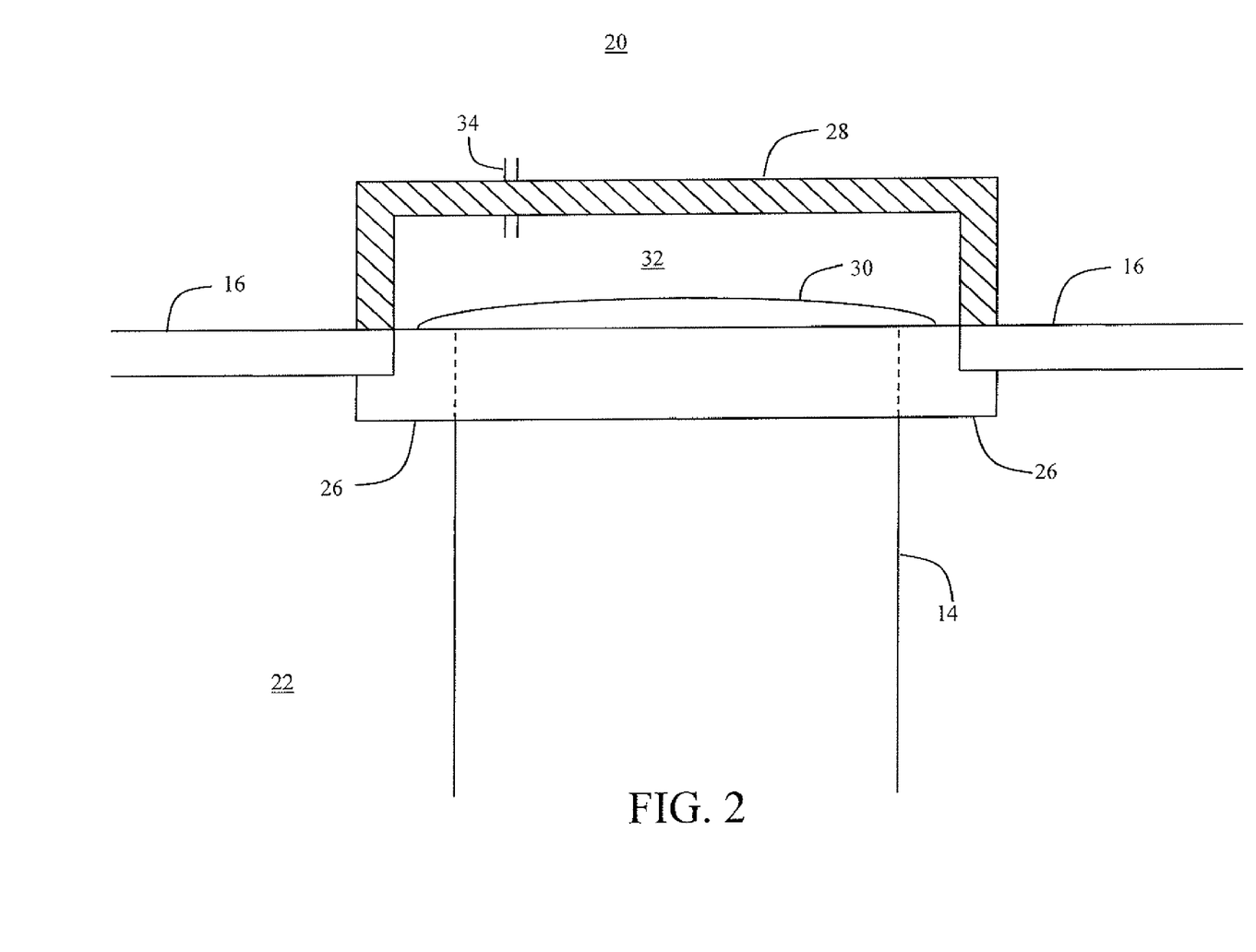
FIG. 2 is a close up view of a containment tube interface.

In the previous embodiment, once the hot side 20 goes hot, the tube 14 is in place and should not be removed before decontamination. Prematurely removing the tube 14 runs the risk of contaminating the cold side 22. Referring now to FIG. 2, the tube 14 is attached to the barrier wall 16 from the cold side 22. Before the tube 14 is attached to the wall 16, a portal cover 28, accessible from the hot side 20 is in place to keep the hot side 20 isolated from the cold side 22. The sealing interface 26 of the tube 14 fits snugly against the barrier wall 16 to isolate it from the cold side 22. Once the tube 14 is in place, the portal cover 28 can be removed from the hot side 20 and the subject can be inserted into the tube 14 as in the previous embodiment. This embodiment has the added advantage of being able to add a containment tube 14 from the cold side 22 after the hot side 20 has already gone hot. It is contemplated that the tube 14 can then remain in place until the hot side 20 is decontaminated.

Alternatively, once the tube 14 is attached, and the tube 14 is no longer needed, a tube cap 30 can seal the tube opening from the hot side 20. Next, the portal cover 28 is replaced over the tube cap 30, sealing off the hot side from the tube 14. In this embodiment, an air gap 32 is left between the portal cover 28 and the tube cap 30. Through a decontamination fluid valve 34 in the portal cover 28, decontaminate can be introduced into the air gap 32 decontaminating the face of the tube cap 30 that faces the air gap 32, and decontaminating the face of the portal cover 28 that faces the air gap 32 and the cold side. Thus, with the outside of the tube 14 and the tube cap 30 decontaminated, and the side of the portal cover 28 that faces the cold side 20 also decontaminated, the tube 14 can be removed from the barrier wall. The inside of the tube 14 itself would be decontaminated at a later time. Alternately, disposable tubes can be used, and replaced with replacement tubes each time an old tube is removed. This embodiment has the advantage of being able to remove the tube 14 from the wall 16 before the hot side 20 is decontaminated without contaminating the cold side 22.

Figure 3:
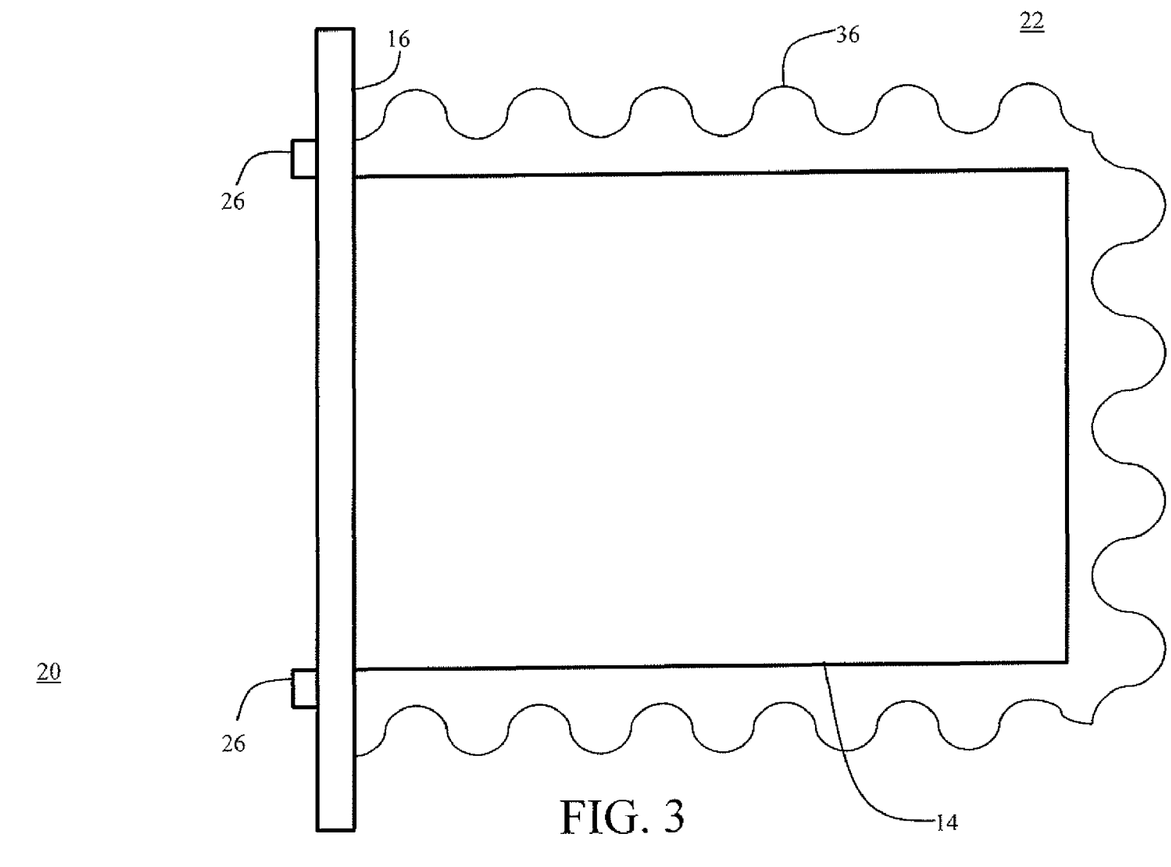
FIG. 3 is a top down view of a containment tube accompanied by a containment shroud.

With reference now to FIG. 3, another embodiment of the containment tube is provided. In this embodiment, the rigid containment tube 14 is attached to the wall 16 from the hot side 20. A flexible containment shroud 36 is attached to the wall 16, e.g. from the cold side 22. In this embodiment, tubes 14 can be attached and detached from the hot side 20 freely, as the shroud 36 maintains the isolation between the sides. When no tube 14 is in place, the shroud 36 can be collapsed and is stored near the wall 16 without being detached, and without breaking containment. As with the tube 14 itself, the shroud 36 is made of a material that is transparent to the modality with which it is being used.

Figure 4A:
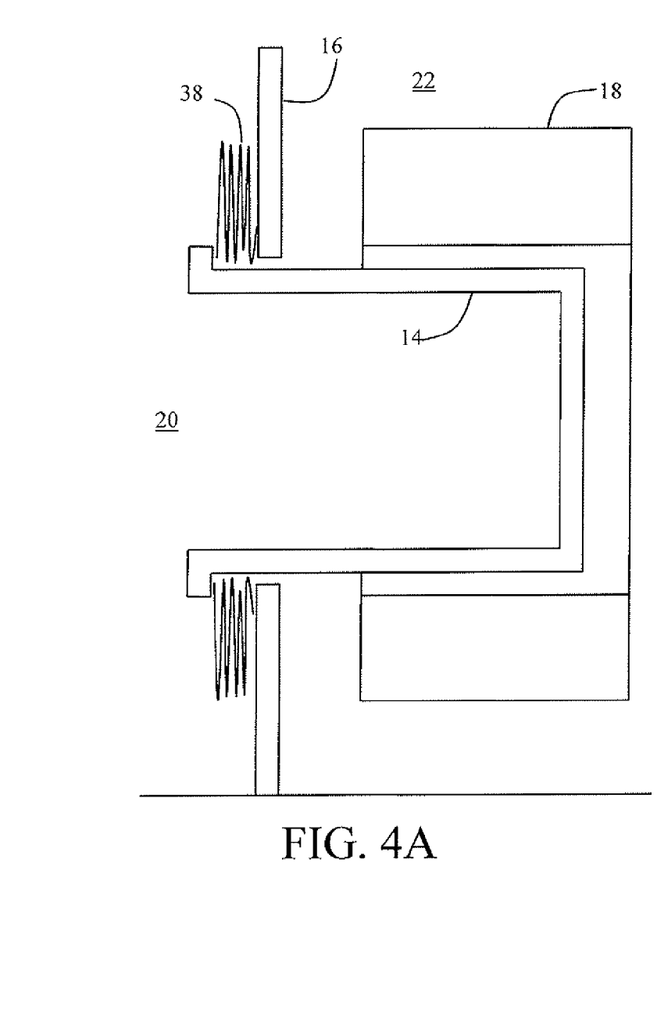
FIG. 4A is a top down view of a containment tube with extensible containment bellows in a deployed position.
Figure 4B:
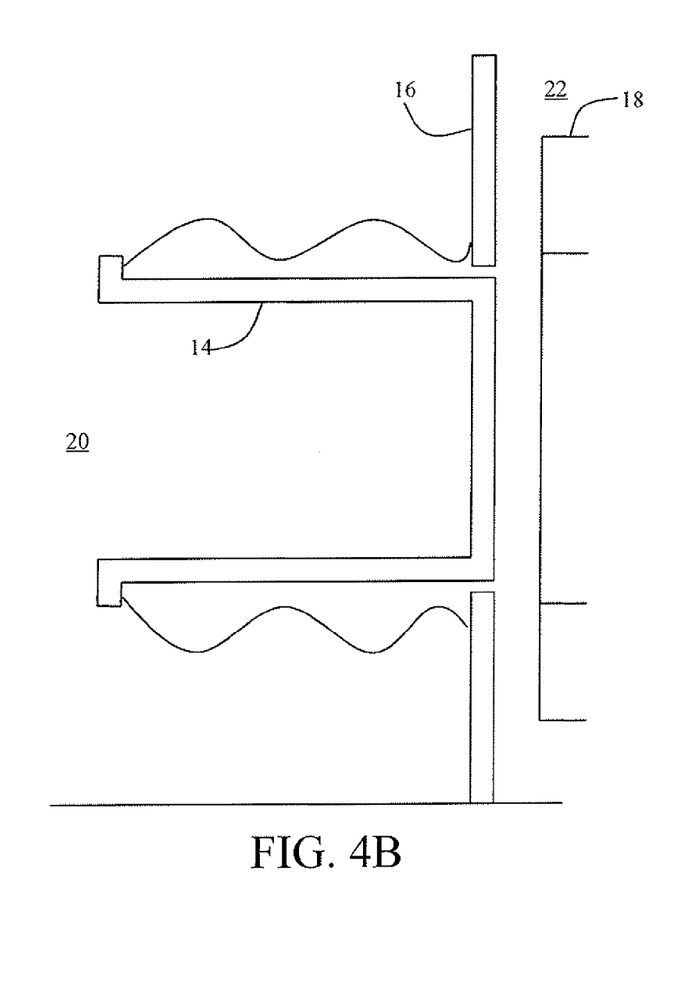
FIG. 4B is a top down view of the tube of FIG. 4A in a retracted position.

With reference now to FIGS. 4A and 4B, another embodiment of the tube 14 is provided. In this embodiment, the tube 14 is slideably connected to the barrier wall 16. A flexible bellows 38 circumscribes the tube 14 providing a containment seal between the tube 14 and the barrier wall 16. This embodiment allows the medical device to quickly go from cold subject scanning to hot subject scanning. When a hot subject requires scanning, the tube 14 is extended into the bore of the gantry 18 as shown in FIG. 4A. The bellows 38 is contracted to allow this motion. When the device is to be used normally, the tube 14 is retracted back through the barrier wall 16 into the hot side 20 freeing the gantry 18 for normal usage. In this configuration, as depicted in FIG. 4B, the bellows 38 is extended to nearly the length of the tube 14. In both the extended and retracted positions, the bellows 38 maintains the seal between the tube 14 and the barrier wall 16. It should be noted that the bellows 38 does not pass through the barrier wall 16, and thus does not go into the gantry 18. Resultantly, the selected material for the bellows does not have to be transparent to the imaging modality with which it is being used, but can be selected for its flexibility, strength, ease of decontamination, and the like.

Figure 5A:
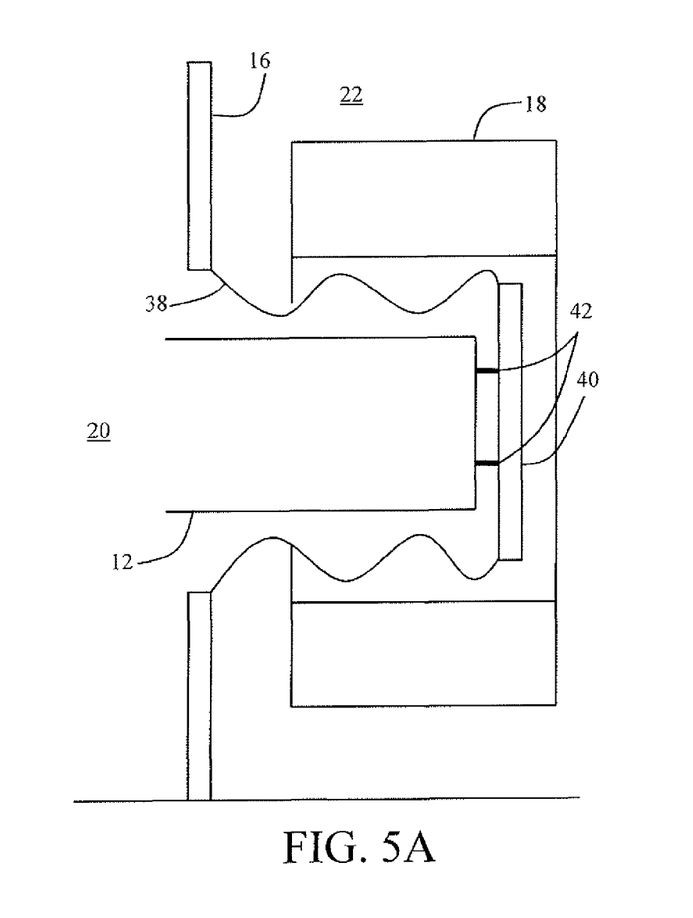
FIG. 5A is a top down view of a non-rigid containment bellows with a rigid end cap in a deployed position.
Figure 5B:
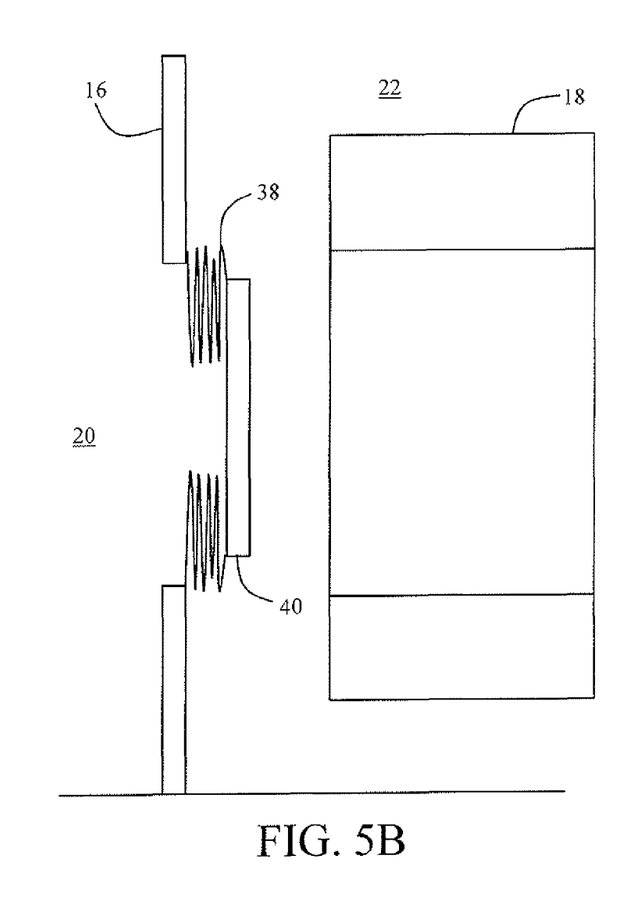
FIG. 5B is a top down view of the bellows of FIG. 5A in a retracted position.

With reference now to FIGS. 5A and 5B, another embodiment is provided. Similar to the previous embodiment, a flexible bellows 38 provides the containment seal with the barrier wall 16. Rather than a containment tube, the bellows 38 is connected to an end cap 40, e.g. a rigid end cap, at one end and to the barrier wall 16 at the other end. The bellows 38 itself functions as the tube 14 of FIGS. 4A and 4B. The bellows 38 is extended into the bore of the gantry 18 for scanning a hot subject, as depicted in FIG. 5A, and is retracted and stored when normal use of the medical device is desired. A latching device 42 can engage the subject support 12 and provide support for the end cap 40 and the bellows 38 as the bellows 38 is deployed. Since the bellows 38 will be in the bore of the gantry 18 during imaging, the material of the bellows 38 is selected to be transparent to the imaging modalities with which it will be used. The bellows 38 can also be optically transparent to allow viewing of the anatomy of the subject during imaging. Again, this embodiment has the flexibility of quick conversion from hot subject scanning to normal use of the medical device.

Figure 6:
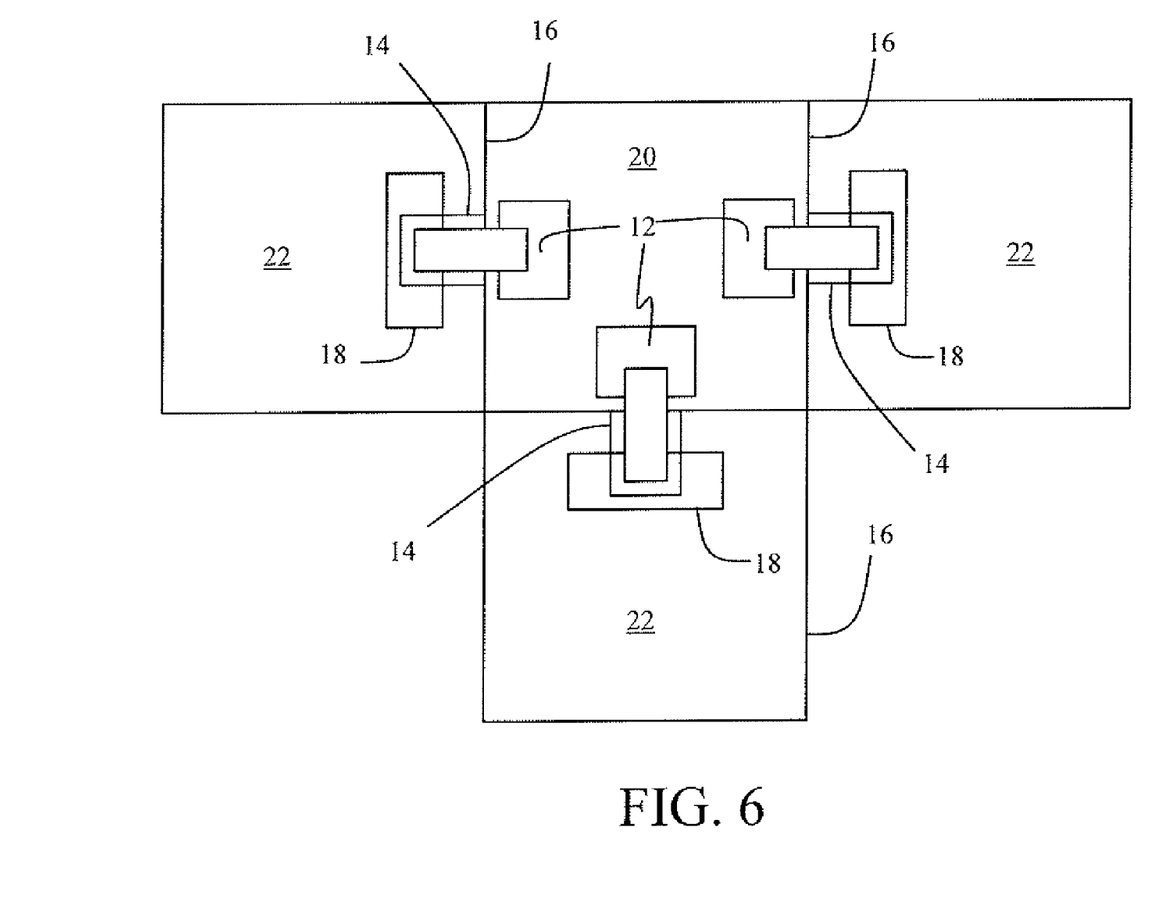
FIG. 6 is an overhead view of one possible room configuration.
Figure 7:
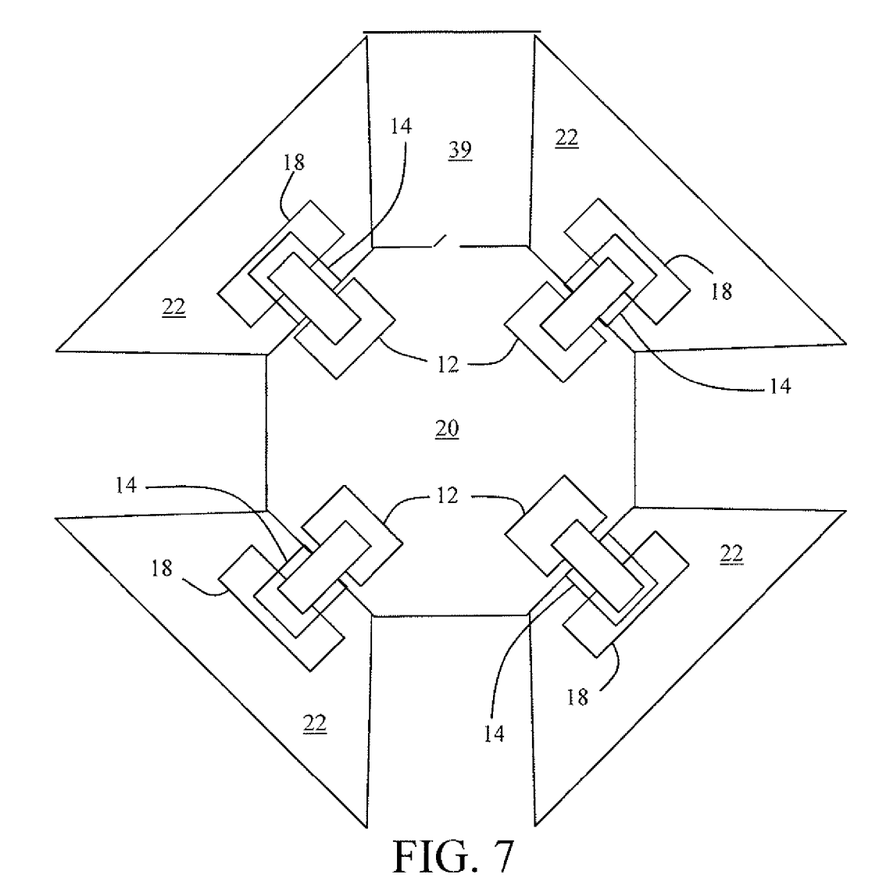
FIG. 7 depicts a second possible room configuration.

Any of the above-described embodiments can be used in a room setup such as the one depicted in FIG. 6. In FIG. 6, there are three distinct cold zones 22 and one hot zone 20. Each of the cold zones 22 is separated from the hot zone 20 by a barrier wall 16 as described in the previous embodiments. There may be a subject support 12 for each barrier wall 16 as depicted, or there may be a single subject support 12 that can rotate, translate, or some combination thereof, between the barrier walls 16. Multiple supports 12 can support parallel imaging of multiple hot subjects in different modalities. As described above, each barrier wall 16 has an aperture through which one of the above-described containment tubes 14 can pass. In FIG. 6, three cold zones 22 are accessible from the hot zone 20. In FIG. 7, the shape of the hot zone 20 is changed to provide simultaneous access to more cold zones, such as four cold zones. A greater number of cold zone rooms 22 are clearly possible, depending on space constraints and accessibility to the tube 14. FIG. 7 also illustrates an entrance/exit interface 39, such as a changing room, which enables medical personnel to change into and out of HAZMAT suits to enter and exit the hot side 20 safely.

Figure 8:
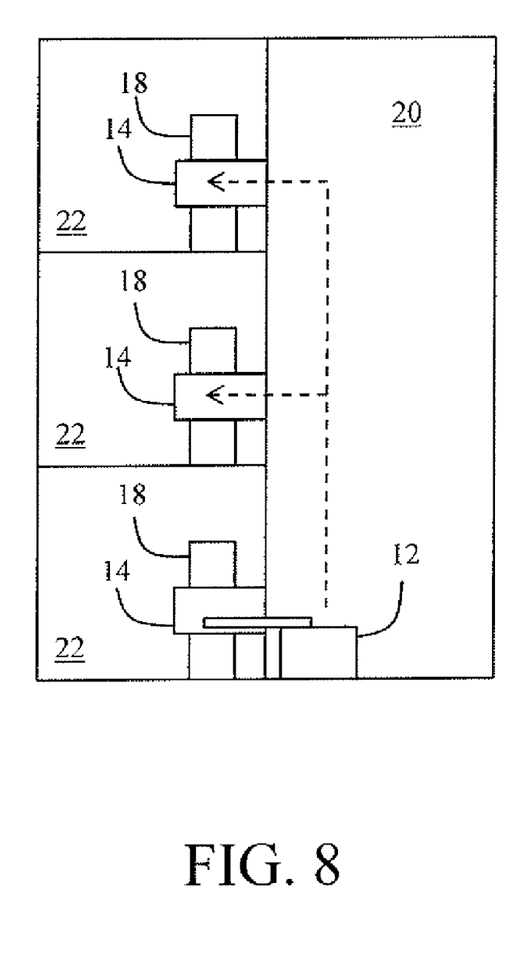
FIG. 8 depicts a vertical scan room configuration.

The medical devices are not constrained to a single floor of a medical facility. With reference now to FIG. 8, cold zones 22 are stacked on top of one another, such as on different floors of a medical facility. Each cold zone is adjacent to a hot zone 20. In the depicted embodiment, the hot zone 20 spans three stories. The subject support can be elevated to interface with the containment tubes 14 of any of the cold zones 22. All of the previously described concepts still apply in a vertically oriented arrangement.

Figure 9:
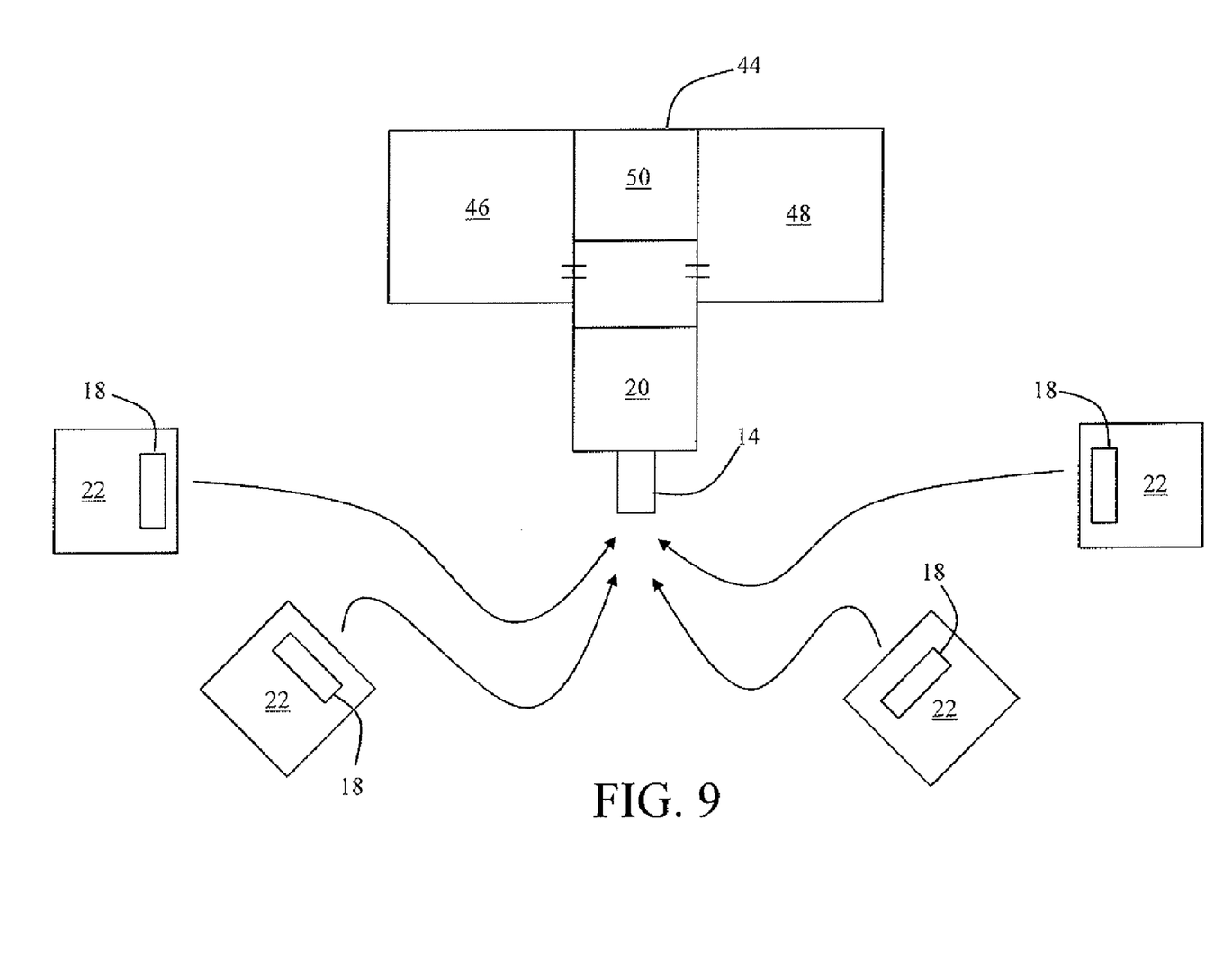
FIG. 9 depicts one possible embodiment of mobile field imaging units and a mobile quarantine facility.

Adding to the concepts described above, it is further contemplated that the hot zones 20 or the cold zones 22 or both, are mobile. The cold zone medical devices can be mounted in vehicle trailers, movable room modules or pods, individually movable for movement within a medical facility, or the like. With reference now to FIG. 9, the hot zone 20 and the cold zones 22 are modular elements, each being movable. In the depicted embodiment, the cold zones 22 each contain a different medical device. When needed, the module can be moved adjacent to the barrier wall 16 of the hot zone 20. Once the selected cold zone is in place, the medical device within the module can be used as described in any of the preceding embodiments. Any physical arrangement, such as the ones depicted in FIGS. 6-8 can be used in this modular setting.

Such an arrangement can be used in a field quarantine setting. A quarantine structure 44, such as a biocontainment tent or a mobile barracks, can be used as subject holding facility for quarantined subjects. The quarantine area 44 can be further subdivided. For instance, in a field quarantine facility, there may be subjects that are confirmed to be contaminated, and subjects who may have been exposed to the contaminant, but it is unsure whether they are themselves contaminated. To avoid risk of contaminating healthy subjects, a confirmed quarantine area 46 is separate from a exposed quarantine area 48. This way, uncontaminated subjects are not forced to risk further exposure by being held with confirmed contaminated subjects. The quarantine structure 44 can also include a decontamination chamber 50 so that subjects and personnel exiting the quarantine structure 44 do not carry contaminants with them. The decontamination chamber can include a chemical shower, or other suitable human decontamination device.

Figure 10:
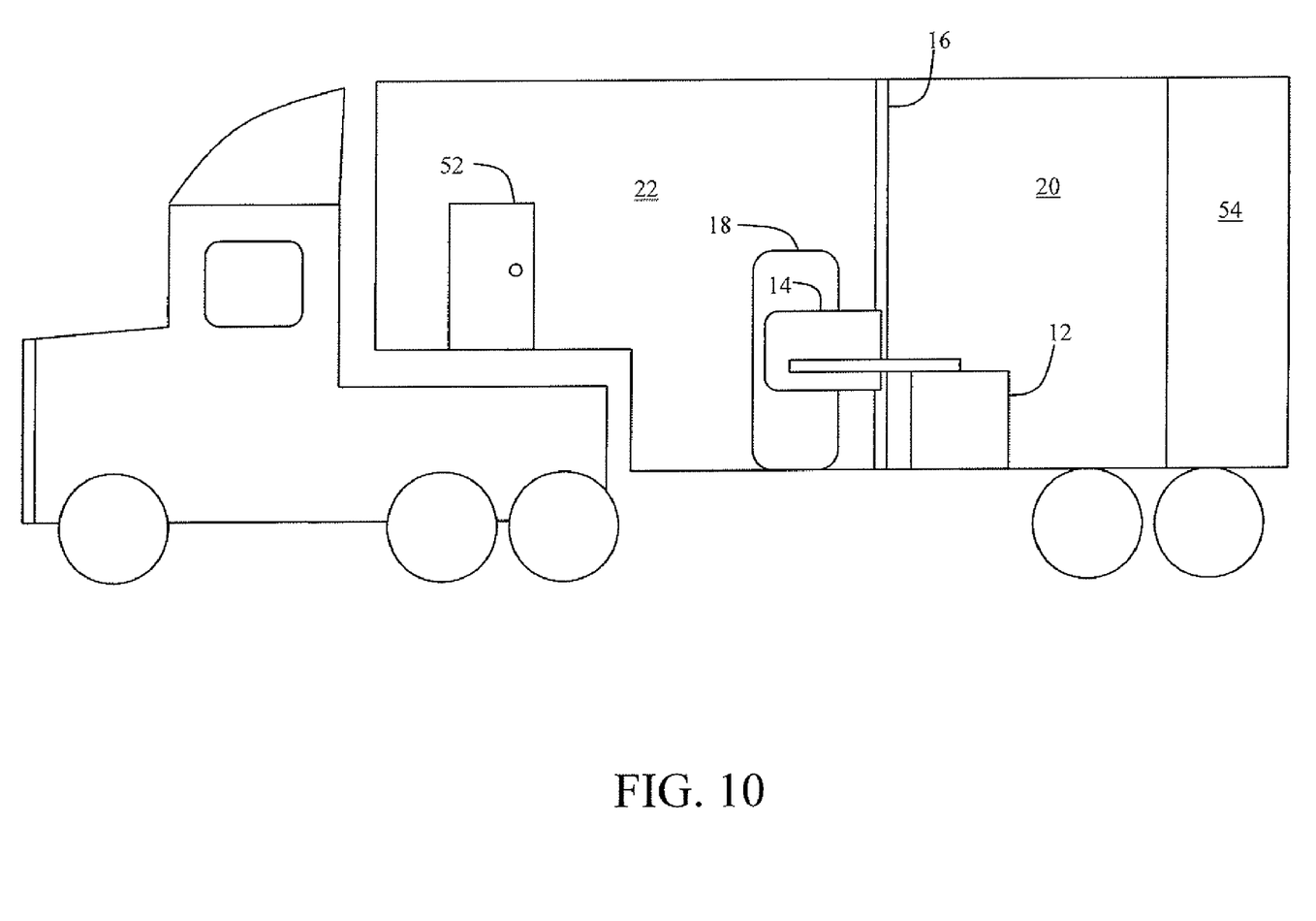
FIG. 10 is a cut away view of a truck trailer embodiment of an isolated imaging modality.

In another mobile embodiment, as depicted in FIG. 10, the hot and cold zones 20, 22 are located in the trailer of a semi truck. A door 52 can be provided for ease of access to the cold side 22, and a decontamination chamber 54 can be used in a similar fashion as the decontamination chamber 50 in the previous embodiment. Another possible extension is to have multiple trailers, some hot and some cold, and they can be connected when it comes time to use them.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An imaging suite comprising:
   a barrier wall for separating a biohazard containment region from an uncontaminated region, the barrier wall including an aperture;
   a selectively deployable containment vessel removably mounted to the barrier wall such that in a deployed configuration the containment vessel is sealed to the barrier wall around the aperture and extends from the biohazard containment region into the uncontaminated region;
   a gantry of a medical imaging device located in the uncontaminated region with an imaging region that is substantially coaxial with a longitudinal axis of the containment vessel such that in the deployed configuration, the containment vessel extends into the gantry and in an undeployed configuration the containment vessel is not in the gantry such that the gantry is available for imaging uncontaminated subjects;
   a subject support for supporting a subject and in a deployed configuration inserting a potentially contaminated subject from the biohazard containment region into the containment vessel and into the gantry and withdraws the subject from the containment vessel in an undeployed configuration;
   a cap configured to seal an opening to the containment vessel with the subject support in the undeployed configuration;
   a portal cover configured to seal the aperture in the barrier wall with the subject support in the undeployed configuration such that when the containment vessel is to define an air gap between the portal cover and the cap, the air gap being configured to receive a decontamination fluid.

2. The imaging suite as set forth in claim 1, wherein the gantry is movably mounted for movement toward and away from the barrier wall.

3. The imaging suite as set forth in claim 1, wherein the containment tube is configured to be removed from the barrier wall into the uncontaminated region after the portal cover has sealed the aperture and the portal cover includes a decontamination fluid valve which releases decontamination fluid to decontaminate faces of the cap and the portal cover which face the air gap.

4. The imaging suite as set forth in claim 1, further including:
a plurality of uncontaminated regions, each with a corresponding barrier wall, deployable containment vessel, gantry, and subject support.

5. The imaging suite according to claim 4, wherein the plurality of uncontaminated regions are mobile structures.

6. The imaging suite as set forth in claim 1, wherein the gantry is configured to image uncontaminated subjects in the uncontaminated region without the containment vessel before and after the containment vessel is deployed and the potentially contaminated subject is inserted into the gantry without decontaminating the biohazard containment region.

7. The imaging suite according to claim 1, wherein the selectively deployable containment vessel supports a BSL-4 containment level in a deployed configuration which maintains the uncontaminated region at a higher pressure than the biohazard region, and seals to the barrier wall such that a controlled flow is permitted from the uncontaminated region to the biohazard region.

8. A method of diagnostic imaging comprising:
removably disposing a containment tube in a deployed configuration surrounding and extending from an aperture in a barrier wall into a gantry of a diagnostic imaging device, which is located in an uncontaminated region adjacent the barrier wall;
disposing a subject on a subject support in a contaminated region;
moving the subject support at least partially into the containment tube to a place at least a portion of the subject in the gantry;
imaging the subject with the diagnostic imaging device;
after imaging the subject:
affixing a tube cap to the containment tube sealing the containment tube from the contaminated region;
affixing a portal cover over the aperture in the barrier wall creating an air gap between the tube cap and the portal cover;
decontaminating the air gap and surfaces of the portal cover and the tube cap facing the air gap; and
removing the tube from the barrier wall after decontaminating the air gap.

9. The method as set forth in claim 8, further including:
imaging uncontaminated subjects in the uncontaminated region with the diagnostic imaging device before and after imaging the first subject without decontaminating the diagnostic imaging device.

10. The method as set forth in claim 9, further including:
before imaging the uncontaminated subjects, removing the subject support and the first subject from the containment tube and retracting the containment tube from the gantry of the diagnostic imaging device.

11. The method as set forth in claim 8, further including:
moving the gantry of the diagnostic imaging device away from the containment tube and moving an uncontaminated second diagnostic imaging device to receive the containment tube in an imaging region of the second diagnostic imaging device.

12. The method as set forth in claim 8, wherein the step of removably disposing the containment tube to the deployed configuration includes:
affixing a rigid containment tube to the barrier wall, forming a seal between the containment tube and the bather wall.

13. The method as set forth in claim 8, wherein the step of decontaminating the air gap includes introducing a decontaminate into the air gap through a decontamination fluid valve with access to the air gap.

14. The method according to claim 8, further including:
removably disposing a second containment tube in a deployed configuration surrounding and extending from a second aperture in the barrier wall into a gantry of a second diagnostic imaging device, which is located in the uncontaminated region adjacent the barrier wall;
disposing a second subject on a second subject support in the contaminated region;
moving the second subject support at least partially into the second containment tube to place at least a portion of the second subject in the gantry of the second diagnostic imaging device; and
imaging the second subject with the second diagnostic imaging device.

15. An imaging structure for imaging subjects, comprising:
a hot chamber for receiving subjects exposed to a biohazard, the hot chamber including:
at least one subject support for supporting a subject during a medical procedure;
a plurality of barrier walls, each barrier wall having an aperture through which a portion of the subject support can pass; and
a containment tube for each aperture of each barrier wall adapted to extend the hot chamber beyond the barrier walls; and
a plurality of cold areas, which are isolated from subjects exposed to the biohazard, each cold area including:
a medical imaging device having a gantry that defines an imaging region aligned with the containment tube such that the containment tube can extend the hot chamber into the imaging region of the medical imaging device without contaminating the cold areas;
wherein each containment tube is attachable to the barrier wall from one of the cold areas and further including:
a sealing interface which provides a seal between the tube and the barrier wall;
a cap configured to close a patient receiving opening to the containment tube with the at least one subject support undeployed; and
a portal cover disposed in the hot chamber and configured for attachment to the barrier wall to seal the aperture in the barrier wall with the at least one subject support undeployed, such that the containment tube is detachable from the barrier wall without contaminating the cold areas.

16. The imaging structure as set forth in claim 15, wherein the hot chamber is a mobile structure.

17. The imaging structure as set forth in claim 15, wherein the plurality of cold areas are mobile structures.

* * * * *